US006055988A

United States Patent [19]

Perisho

[11] Patent Number: 6,055,988

[45] Date of Patent: May 2, 2000

[54] BACKBOARD

[76] Inventor: Jack Perisho, 26671 Granvia Dr., Mission Viejo, Calif. 92691

[21] Appl. No.: 09/229,451

[22] Filed: Jan. 12, 1999

[51] Int. Cl.[7] .................................................... A61B 19/00

[52] U.S. Cl. ................................ 128/869; 128/870; 5/628

[58] Field of Search .................................... 128/845, 846, 128/869, 870; 5/628, 621, 624, 625

[56] References Cited

U.S. PATENT DOCUMENTS

| | | | |
|---|---|---|---|
| 4,064,574 | 12/1977 | Schnitzler | 5/628 |
| 4,945,583 | 8/1990 | Schnitzler | 5/628 |
| 5,014,724 | 5/1991 | Miller | 5/82 R |
| 5,414,883 | 5/1995 | Fungrow | 128/870 |
| 5,492,285 | 2/1996 | Hamrick | 242/379 |

*Primary Examiner*—Michael A. Brown
*Attorney, Agent, or Firm*—Stefan J. Kirchanski, Esq; Graham & James LLP

[57] ABSTRACT

An improved backboard contains hollow channels or "tunnels" embedded in the board and accessible from the edges and lower surface of the board. Such channels are preferably integral to the device and do not lessen the strength of the board. Patient straps and restraining devices are conveniently stored within the channels in a more or less fully elongated state so that they can be quickly retrieved for restraining a patient. Because the straps are stretched out as opposed to rolled or otherwise packaged, they can be quickly deployed with a minimum of twisting or tangling.

4 Claims, 6 Drawing Sheets

FIG. 3
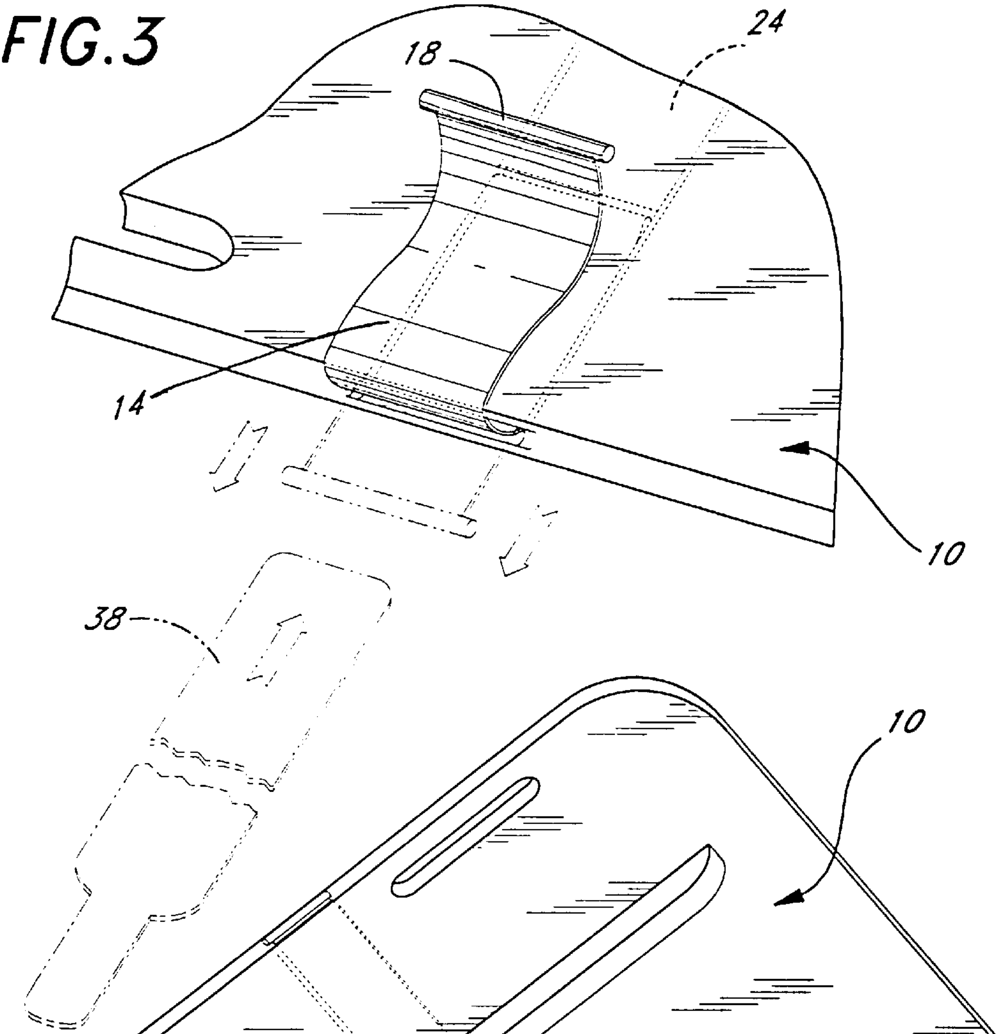
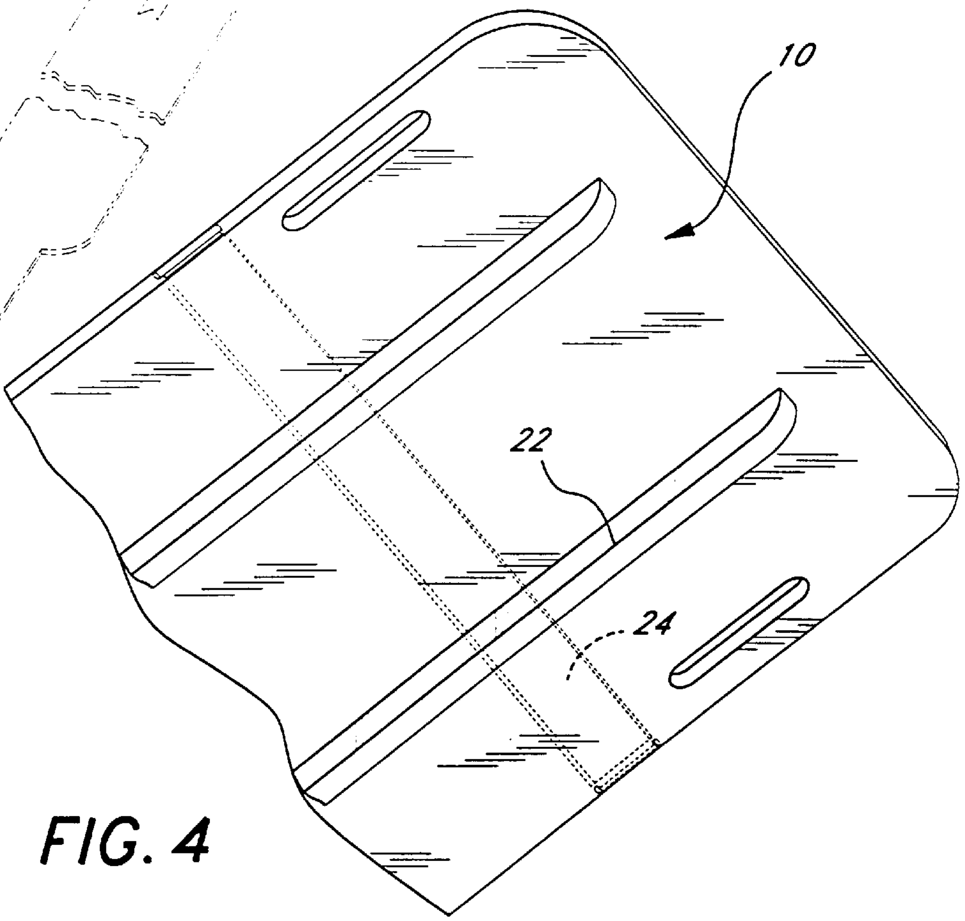
FIG. 4

BACKBOARD

BACKGROUND OF THE INVENTION

1. Field of the Invention

The present application concerns the field of emergency medical treatment and more particularly deals with an improved backboard or stretcher for use in safely transporting injured patients.

2. Description of Related Art

When an individual receives a traumatic injury in an automobile accident or similar mishap, survival often depends on rapid attention from emergency medical personnel followed by immediate transport to a properly equipped hospital. The emergency medical personnel who are first at the scene of the accident are responsible for treating any immediately life-threatening injuries and for stabilizing the patient for immediate transit to the hospital. One of the most vexing problems faced by these workers is that of neck and back injuries to the victim. Without an x-ray it is often impossible to determine the extent, if any, of the damage. If the spine is damaged, the very act of moving the patient may exacerbate the problem and lead to more extensive spinal injury.

There has been some controversy over the best way to treat these injuries prior to transport. Some authorities favor immobilizing the patient's neck and back in the orientation in which the patient was found. Other authorities favored moving the patient into a neutral position prior to immobilization. Today most practitioners follow the second option and immobilize the patient in a neutral position.

A number of devices and procedures have been developed to immobilize accident victims in a neutral position and allow transport with little or no danger of causing additional spinal damage. The common factor in most of these devices is the simple expedient of firmly attaching the patient to the surface of an stiff, inflexible "board" (backboard) which acts as a stretcher to allow the patient to be carried without allowing any flexing of the patients potentially injured back and neck. By "transport" is meant, of course, moving the immobilized patient to a hospital, but transport also includes moving the patient from the accident site to the transport vehicle (e.g., ambulance or helicopter). It is not uncommon that the victim will be in a ravine or some similarly inaccessible location.

This means that the emergency medical personnel must leave the vehicle and carry their equipment, including a backboard, to the site of the accident. Then the patient is freed from the accident debris, if necessary, placed on and secured to the backboard and then carried back to the transport vehicle. For these reasons the backboard must be relatively light while providing rigidity to avoid flexure during carrying of the patient. The backboard must also be equipped with straps or other hold-down devices so that the patient is immobilized and does not move around during the, sometimes rough and difficult, move from the accident site to the transport vehicle. These same immobilization devices also protect the patient from movement during vehicular transport back to the hospital. The ride in a speeding ambulance can be rough. Therefore, all steps must be taken to avoid exacerbation of the patient's injuries due to bouncing around.

A variety of backboards and similar devices have been developed to fill the need for a rigid, light and easy to use immobilization system for moving the injured. Typical of these devices is that disclosed in U.S. Pat. No. 5,088,137 to Rose. The device is a typical rigid board to which a removable pad can be strapped to provide a cushion between the patient and the board. The straps that immobilize the patient can be attached to the pad so that a single strap/pad unit is formed. U.S. Pat. No. 4,566,445 to Jelsma et al. discloses a composite material board with quick disconnect devices for attaching a plurality of patient immobilization straps. A pediatric immobilization board is shown in U.S. Pat. No. 5,014,724 to Miller. That device comes equipped with a plethora of immobilizing straps and similar structures attached to an upper surface thereof.

These and similar devices common to the art consist of a rigid board and a separate assortment of straps. The problem common to these devices is where to put the straps prior to use? Ambulances and similar emergency vehicles are not known for their spacious interiors. Generally, the backboards are stacked and inserted into suitable compartments or niches in the vehicle. If the boards come with a preattached strap system as appears to be contemplated by devices such as that disclosed by Miller, the straps may prevent efficient stacking of the boards and make it difficult to store an adequate supply of backboards in the vehicle. If the straps are removed for storage so that the boards can be readily stacked, there can be a considerable delay in locating the stored straps and installing them on the board. Such a delay can mean the difference between life and death for a critically injured patient. Not only is there potential for delay, the emergency medical personnel may carry the board and straps to an inaccessible accident location only to discover that they have failed to bring a full complement of straps and similar attachment devices.

OBJECTS AND SUMMARY OF THE INVENTION

It is an object of the present invention to provide an improved lightweight backboard that can be easily stacked for storage.

It is a further object of the present invention to provide a backboard with convenient storage means for a full complement of straps or other patient restraining devices.

These and additional objects are met by a backboard that contains hollow channels or "tunnels" embedded in the board and accessible from the edges and lower surface of the board. Such channels are preferably integral to the device and do not lessen the strength of the board. Patient straps and restraining devices are conveniently stored within the channels in a more or less fully elongated state so that they can be quickly retrieved for restraining a patient. Because the straps are stretched out as opposed to rolled or otherwise packaged, they can be quickly deployed with a minimum of twisting or tangling.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings in which like structures are indicated by like signs.

FIG. 3 illustrates pulling straps from the strap channel of the present invention.

FIG. 4 illustrates the lower surface of one embodiment of the backboard showing the strap channels in phantom.

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved backboard with channels within the body of the board for containing straps and similar patient restraining devices.

Figures 1, 2:
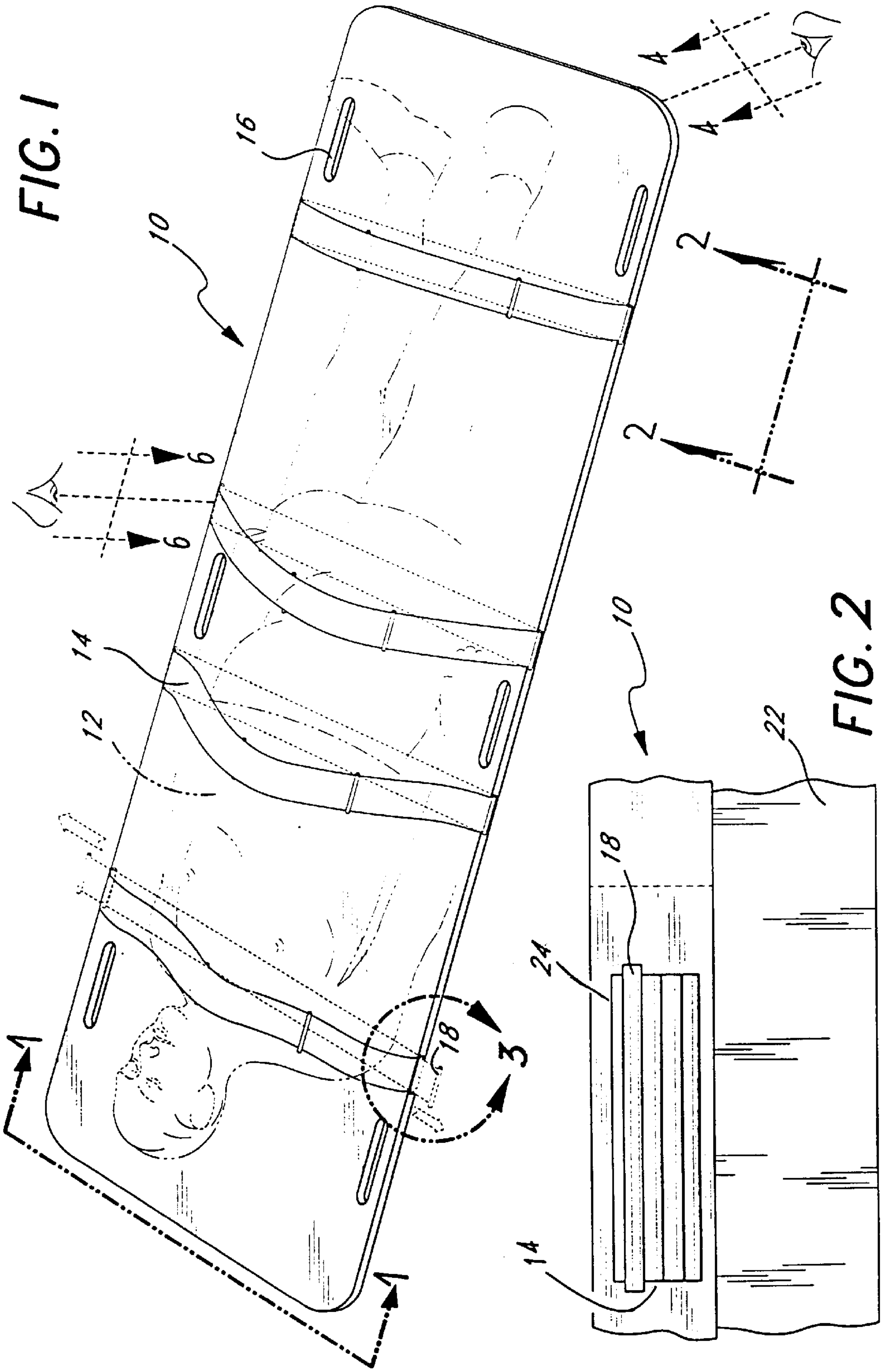
FIG. 1 shows a perspective view of one embodiment of a backboard of the present invention with a restrained patient in phantom.
FIG. 2 shows a side view of a strap channel of the present invention taken at 2—2 of FIG. 1.
Figure 7:
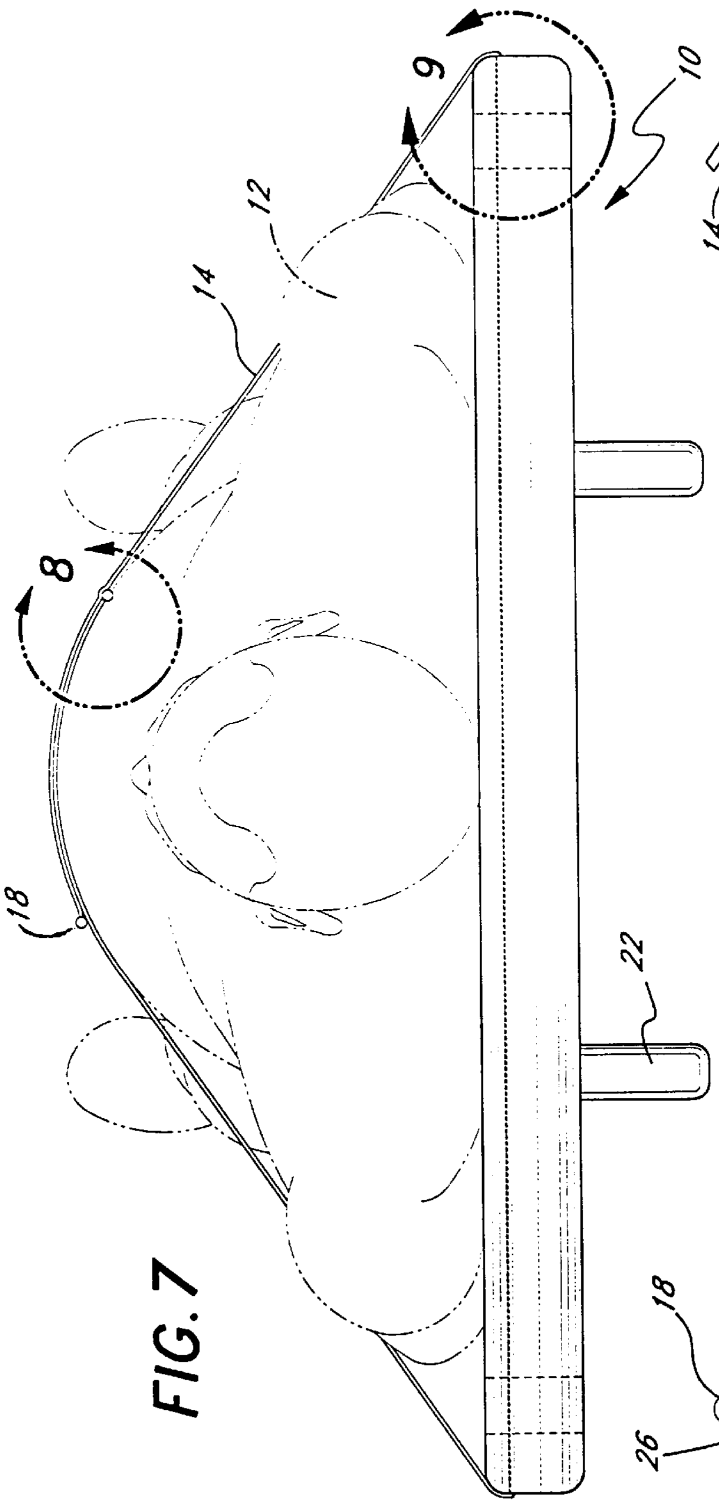
FIG. 7 illustrates an end-on view of a patient restrained on a backboard of the present invention.
Figure 9:
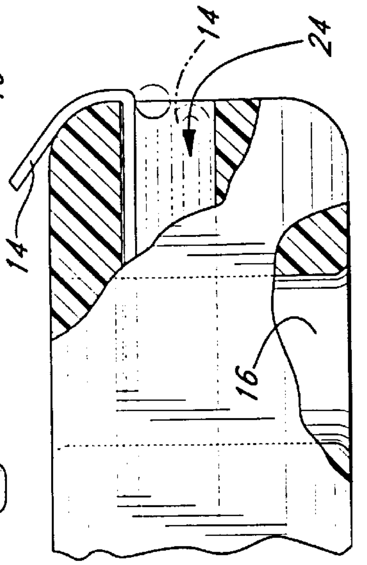
FIG. 9 shows the detail of a folded strap stored in the strap channel of the present invention.

FIG. 1 shows a perspective view of one embodiment of the backboard 10 of the present invention with a patient 12 (phantom) restrained to the device. On first glance the backboard 10 seems typical with handholds 16 for carrying and straps 14 for restraining. As shown in FIG. 7, and in an alternative embodiment in FIG. 5, a pair of longitudinal stiffening rails 22 stiffens the board 10. These rails 22 provide sides to the device (FIG. 2) and allow the unit to sit slightly above a surface upon which it is placed so that the handholds 16 can be easily grasped.

Figure 5:
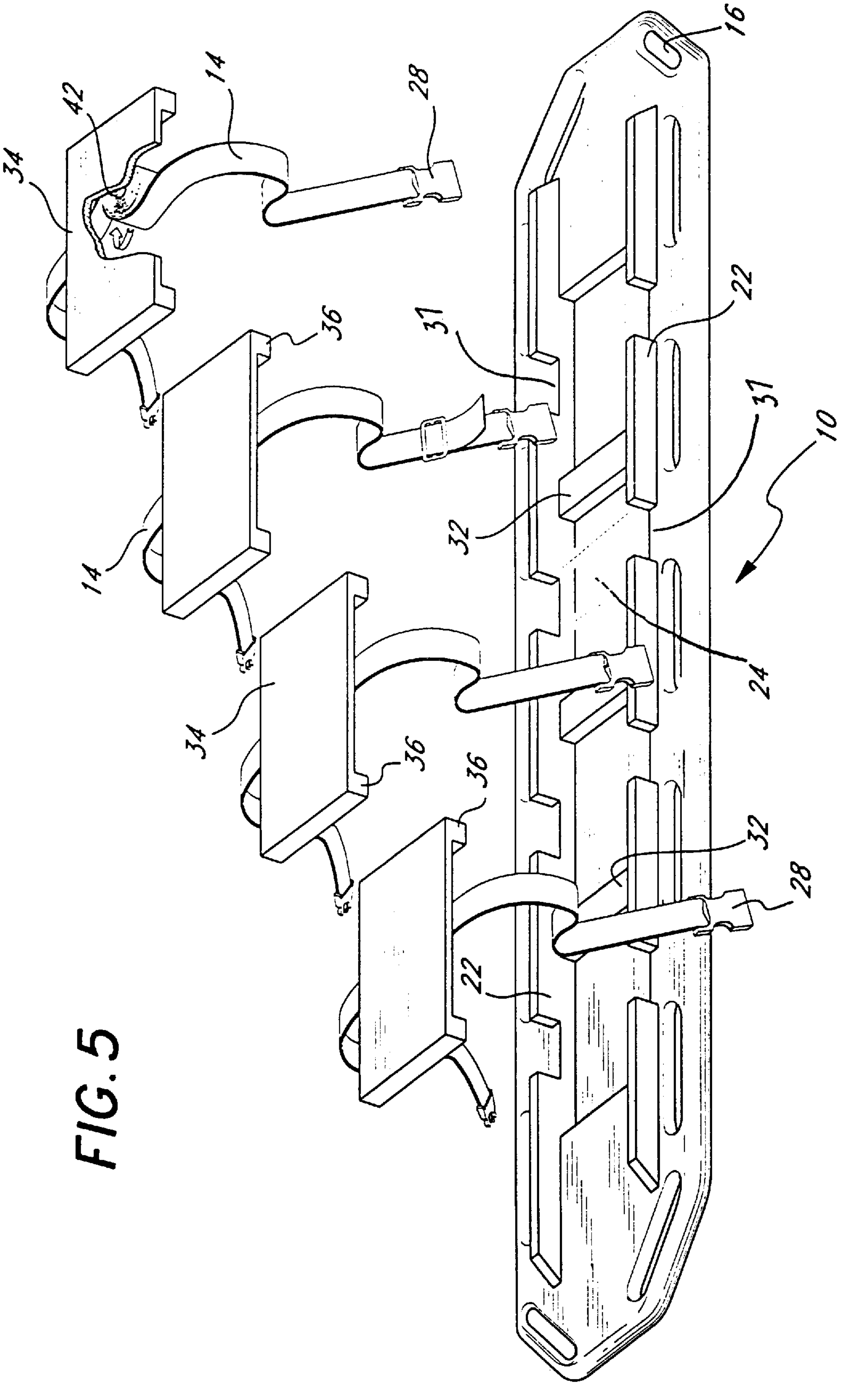
FIG. 5 illustrates an exploded view of the lower surface of one embodiment of the backboard of the present invention illustrating the channel modules.
Figure 6A:
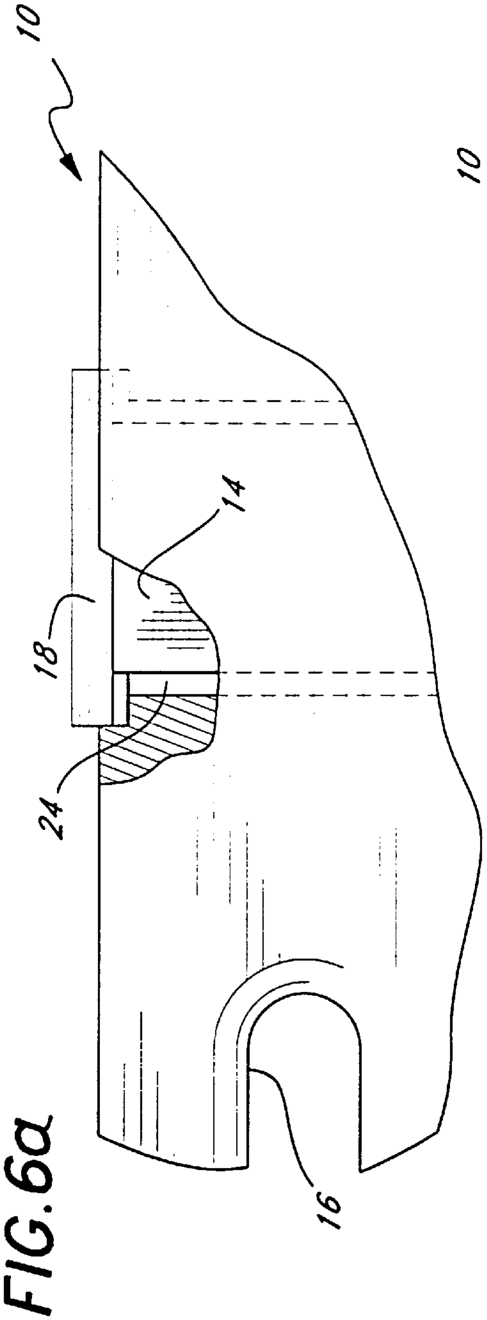
FIG. 6*a* illustrates the end of a strap held in the strap channel of the present invention.
Figure 6B:
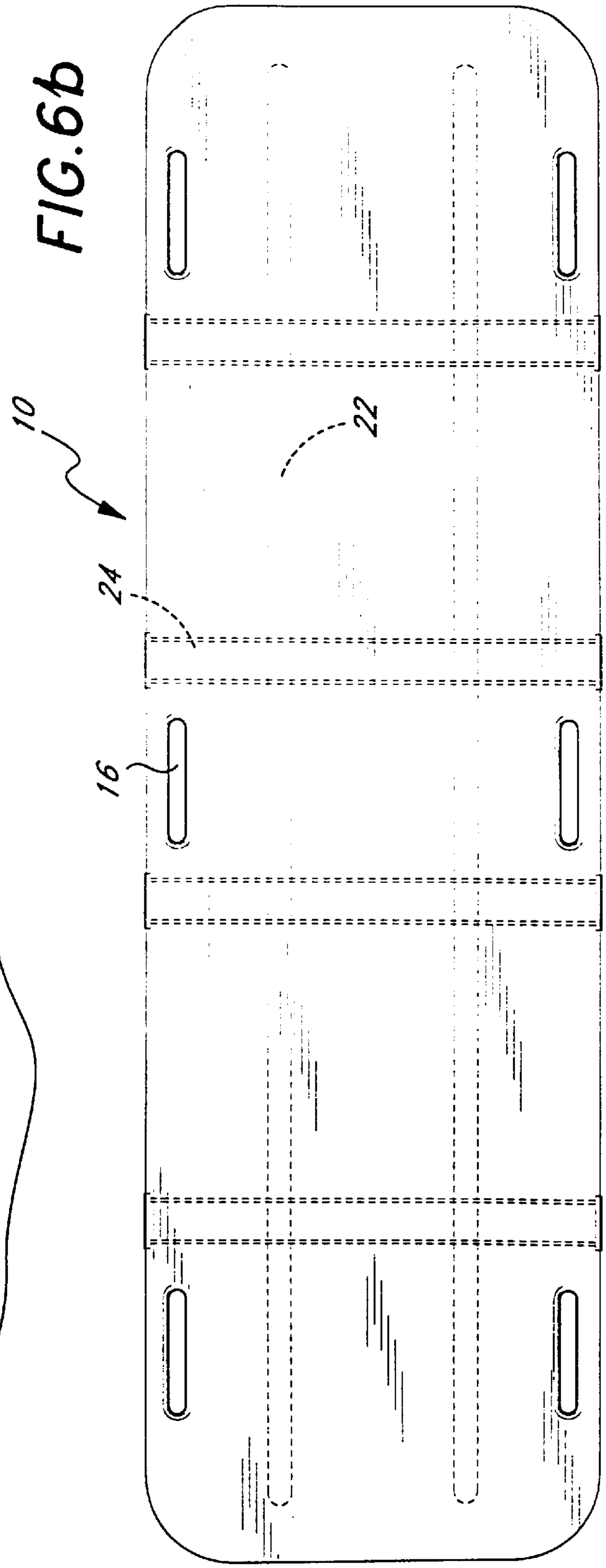
FIG. 6*b* illustrates a top view of the embodiment of FIG. 6*a* with the strap channels in phantom.

As illustrated in FIGS. 3 and 5, a striking difference between this and ordinary backboards is that the straps 14 are not visible on the lower surface of the device 10. Instead the straps 14 are contained within strap channels 24 (phantom in FIG. 4) that are embedded within the board 10. As shown in FIG. 2, the strap end 18 can be seen at the end of the strap channel 24. The strap 14 is neatly folded, or otherwise contained, within the strap channel 24. This allows the board 10 to be readily stacked or moved about with no interference from the straps 14. FIG. 6*a* shows a breakaway of the end 18 of a strap at the edge of the board 10. FIG. 6*b* shows an upper surface of the board 10 of FIG. 6*a* showing (in phantom) how the strap channels 24 pass through (or above) the stiffening rails 22.

Figure 8:
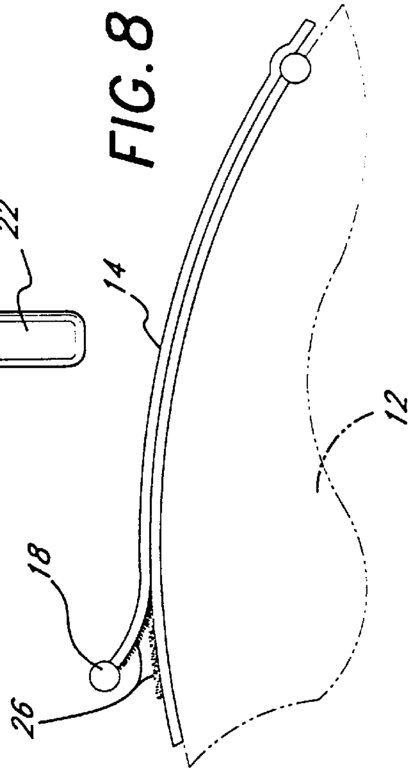
FIG. 8 shows the details of a hook-in-loop fastening used with one embodiment of the present invention.

After the patient 12 is placed on the board 10, the strap ends 18 are easily grasped and the strap 14 pulled out and used to immobilize the patient 12 (FIG. 7). In FIGS. 5, 7 and 8 the straps 14 are equipped with a hook-in-loop fastening system 26 with complementary parts of this system on opposing surfaces of the straps 14. When the strap 14 is pulled out from opposite sides of the board 10, the straps 14 readily adhere to each other as shown in FIG. 8. Alternatively, (FIG. 5) the strap ends 14 can have traditional buckles 28 which are pulled out from the strap channels 24. In this case the terminal ends of the strap channels 28 at or near the rails 22 can be equipped with detents, clips or similar devices to hold the buckles 28 in place until they are pulled from the strap channels 24. In either case each strap 14 is preferably a single strap spanning the width of the board 10 with one end emerging from the strap channel 24 at either side of the board 10. The center of each strap 14 is located at approximately the midpoint (lengthwise) of each strap channel 24 and may be fastened to the channel 24 or the backboard at that point to prevent the strap 14 from being accidentally pulled from the channel 24.

After each use the straps 14 must be stowed in the strap channels 24 awaiting the next use of the board 10. If the channels 24 are permanently affixed to or embedded within the board 10 this can be accomplished through the use of a "pusher" 38 as shown in FIG. 3. However, in a preferred embodiment (FIG. 5) the strap channels 24 are formed from a plurality of channel modules 34, one for each strap channel 24. Each module 34 has the midpoint of one strap 14 fastened to it (alternatively the center of the strap 14 can be fastened to the board 10 beneath the module 34). The modules 34 are sized to snap into place on the underside of the board 10 between the stiffening rails 22 with the ends of the strap 14 passing through notches 37 in the rail 22. Module ends 36 form stand-offs which are sized to be supported by reinforcing struts 32 so that a clearance (the strap channel 24) is formed. With this design the straps 14 are conveniently stowed within the board 10 by placing the board 10 upside down on a surface and temporarily removing each channel module 34. As the module 34 is lowered back into position one doubles the attached strap 14 back and forth within the channel 24. Finally, the module 34 is reattached to the board 10 with the strap 14 stowed within. Alternatively, the strap 14 (or straps) can be attached to the backboard 10 underneath each module 34. In this instance, the straps 14 is readily folded back and forth and then covered by the channel module 34.

FIG. 5 also shows a strap winder 42 which is used to retract the strap 14 without need for folding. The winder 42 can contain a ratcheted spring to automatically retract the strap 14; or the winder 42 can be a simple spool with a removable crank (not shown) inserted into a hole on the board 10 to crank in the strap 14. These arrangements allows the strap 14 to be readily stowed, worn straps to be readily replaced or straps with different buckles or other fastening systems to be substituted whenever needed. Those of ordinary skill in the art can readily imagine other ways to construct the strap channels 24 of the present invention.

Figure 10:
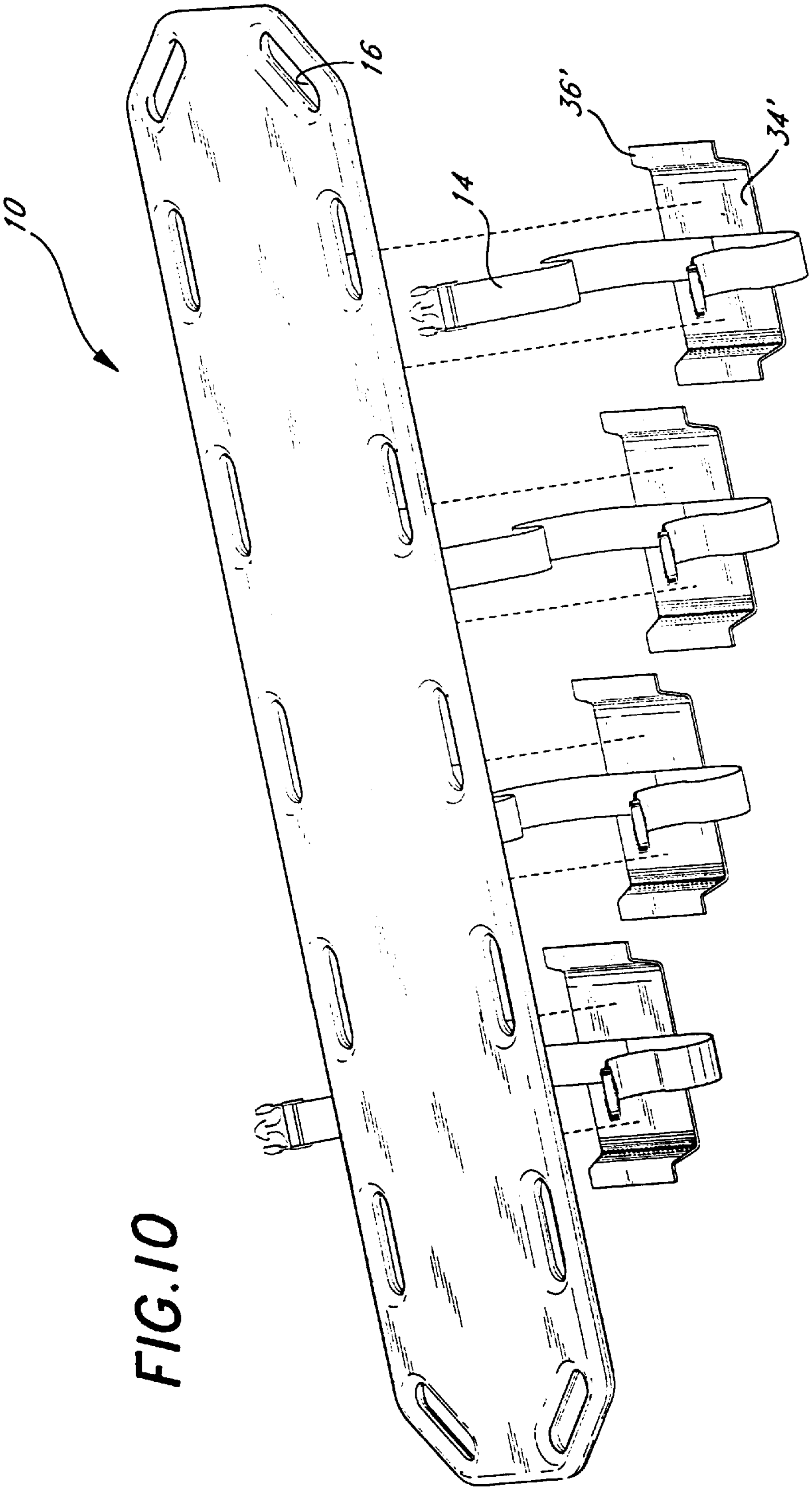
FIG. 10 shows an exploded view from the upper surface of a modular strap channel board similar to the embodiment shown in FIG. 5.

Separate channel units can be attached to the underside of the board 10 preferably within provided recesses so that the profile of the board is not increased. Or the board 10 can be produced in halves so that the entire lower surface can be removed to access the straps. The "strap" may actually represent two straps, one strap for a first side of the board and a second strap for the opposite side of the board with one end of each strap affixed within the strap channel. A variety of board construction methods are possible including plastic injection and fiber-glass/resin composites. A preferred method of fabrication is rotational injection molding of high-density polyethylene or similar thermoplastics. FIG. 5 shows channel modules 34 constructed by such molding. FIG. 10 shows alternative channel modules 34' constructed of bent metal of similar material (notice the "stand-offs" 36').

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A backboard system for immobilizing a patient during transport comprising:

a rigid board member having an upper support surface, longitudinal sides and a lower surface;

a longitudinal rail, within or on the lower surface of the rigid board member, the rail running parallel to the longitudinal sides;

straps for immobilizing a patient placed on the upper support surface; and a channel passing from a first longitudinal side to a second longitudinal side of the board member passing through the rail, and storing at least one of the straps when the strap is not used for immobilizing.

2. The backboard system of claim 1 further comprising retractor means for withdrawing the straps into the channels.

3. The backboard system of claim 1 further comprising a channel module which is a member separable from the rigid board member adapted to engage the backboard system with one of the channels formed within the channel module or between the channel module and the rigid board member.

4. A backboard system for immobilizing a patient during transport comprising:

a rigid board member having an upper support surface, a lower surface, and at least one stiffening rail running a length of the lower surface;

at least one strap for immobilizing a patient placed on the upper support surface; and a channel module forming a passage passing through the rail, from a first longitudinal side to a second longitudinal side of the board member to conceal the strap when the strap is not used for immobilizing.

* * * * *